US010045756B2

(12) United States Patent
Field et al.

(10) Patent No.: US 10,045,756 B2
(45) Date of Patent: Aug. 14, 2018

(54) MEDICAL DEVICES

(75) Inventors: Stephen James Field, Canterbury (GB); Richard Hingley, Hythe (GB); Stephen James Lodge, Colchester (GB); Thomas Cuthbert Mills, Romney Marsh (GB)

(73) Assignee: The Cooper Companies Global Holdings LP, St. Michael (BB)

( * ) Notice: Subject to any disclaimer, the term of this patent is extended or adjusted under 35 U.S.C. 154(b) by 1610 days.

(21) Appl. No.: 10/803,882

(22) Filed: Mar. 19, 2004

(65) Prior Publication Data

US 2004/0193055 A1 Sep. 30, 2004

(30) Foreign Application Priority Data

Mar. 29, 2003 (GB) .................................. 0307350.9

(51) Int. Cl.

| | |
|---|---|
| ***A61B 8/14*** | (2006.01) |
| ***A61B 8/08*** | (2006.01) |
| ***A61L 29/18*** | (2006.01) |
| ***A61M 25/00*** | (2006.01) |
| *A61B 17/435* | (2006.01) |
| *A61B 90/00* | (2016.01) |

(52) U.S. Cl.

CPC .......... *A61B 8/0841* (2013.01); *A61B 8/0833* (2013.01); *A61L 29/18* (2013.01); *A61M 25/001* (2013.01); *A61B 17/435* (2013.01); *A61B 2090/3925* (2016.02)

(58) Field of Classification Search

CPC .......... A61B 17/435; A61B 2019/5425; A61B 8/0833; A61B 8/0841

USPC .......................... 600/437, 458; 424/9.5, 9.52

See application file for complete search history.

(56) References Cited

U.S. PATENT DOCUMENTS

| | | | |
|---|---|---|---|
| 2,702,034 A | 2/1955 | Walter | |
| 2,740,192 A | 4/1956 | Ogle | |
| 2,989,053 A | 6/1961 | Hamilton | |
| 3,093,134 A | 6/1963 | Roehr | |
| 3,605,750 A | 9/1971 | Sheridan et al. | |
| 3,720,210 A | 3/1973 | Diettrich | |
| 4,265,251 A * | 5/1981 | Tickner | 600/438 |
| 4,386,628 A | 6/1983 | Stanley | |

(Continued)

FOREIGN PATENT DOCUMENTS

| | | | |
|---|---|---|---|
| DE | 38 33 365 | 4/1989 | A61B 6/00 |
| DE | 39 36 162 | 6/1991 | A61M 29/00 |

(Continued)

OTHER PUBLICATIONS

Coloreu, B. et al., "Embryo transfer under ultrasound guidance improves pregnancy rates after in-vitro fertilization", *Human Reproduction*, vol. 15, No. 3, pp. 616-620 (2000).

(Continued)

*Primary Examiner* — Baisakhi Roy

(74) *Attorney, Agent, or Firm* — Fish & Richardson P.C.

(57) ABSTRACT

An embryo transfer catheter or other medical device has a shaft extruded with two layers. The outer layer is relatively thick and contains gas bubbles sufficient to increase the visibility of the catheter under ultrasound observation but with a density that allows material within the catheter to be viewed by the eye. The inner layer is relatively thin and is free of bubbles so that it provides a smooth bore to the catheter.

21 Claims, 1 Drawing Sheet

13
III
22
15
14
12
10
III

(56) References Cited

U.S. PATENT DOCUMENTS 4,582,061 A 4/1986 Fry
4,644,977 A * 2/1987 Arterburn .................... 138/137
4,701,161 A 10/1987 Lenck
4,731,052 A 3/1988 Seitz, Jr.
4,805,628 A * 2/1989 Fry et al. ..................... 600/458
4,809,860 A 3/1989 Allen
4,810,244 A 3/1989 Allen
4,824,434 A 4/1989 Seitz, Jr.
4,832,681 A 5/1989 Lenck
4,869,259 A 9/1989 Elkins
4,874,649 A 10/1989 Daubenbüchel et al.
4,877,033 A 10/1989 Seitz, Jr.
4,887,615 A 12/1989 Taylor
5,048,530 A 9/1991 Hurwitz
5,071,425 A * 12/1991 Gifford, III ...... A61B 17/32078 156/294
5,081,997 A * 1/1992 Bosley, Jr. ............ A01K 85/00 424/9.4
5,090,414 A 2/1992 Takano
5,149,328 A 9/1992 Zaha
5,160,319 A 11/1992 Emery et al.
5,195,979 A 3/1993 Schinkel et al.
5,201,314 A * 4/1993 Bosley et al. ............... 600/458
5,211,627 A * 5/1993 William ......................... 604/82
5,250,649 A * 10/1993 Onwumere et al. ........... 528/44
5,259,837 A 11/1993 Van Wormer
5,273,527 A 12/1993 Schatz et al.
5,289,831 A * 3/1994 Bosley .................. A01K 85/00 128/899
5,327,891 A * 7/1994 Rammler ............ A61B 8/0833 600/435
5,342,309 A 8/1994 Hausser
5,360,389 A 11/1994 Chenette
5,383,466 A 1/1995 Partika
5,405,321 A 4/1995 Reeves
5,415,634 A * 5/1995 Glynn et al. ............ 604/103.08
5,596,990 A 1/1997 Yock et al.
5,611,345 A 3/1997 Hibbeln
5,622,665 A 4/1997 Wang
5,646,194 A 7/1997 Kobayashi et al.
5,688,490 A * 11/1997 Tournier ........... A61K 49/1845 424/9.5
5,724,977 A 3/1998 Yock et al.
5,741,522 A 4/1998 Violante et al.
5,744,092 A 4/1998 Halgren et al.
5,759,154 A 6/1998 Hoyns
5,766,135 A 6/1998 Terwilliger
5,769,795 A 6/1998 Terwilliger
5,772,642 A 6/1998 Ciamacco, Jr. et al.
5,820,554 A 10/1998 Davis et al.
5,820,850 A * 10/1998 Hashimoto .......... A61K 49/223 424/9.52
5,827,174 A 10/1998 Reuss, Jr. et al.
5,843,023 A 12/1998 Cecchi
5,851,464 A 12/1998 Davila et al.
5,851,477 A 12/1998 Halgren et al.
5,879,305 A 3/1999 Yock et al.
5,921,933 A * 7/1999 Sarkis ................. A61B 8/0833 600/459
5,932,154 A 8/1999 Csongor et al.
5,932,299 A 8/1999 Katoot
5,939,015 A 8/1999 Csongor
5,945,061 A 8/1999 Csongor et al.
5,967,988 A 10/1999 Briscoe et al.
5,976,501 A * 11/1999 Jablonski ............ A61K 49/223 424/9.52
6,010,448 A 1/2000 Thompson
6,018,676 A 1/2000 Davis et al.
6,024,727 A 2/2000 Thorne et al.
6,027,443 A 2/2000 Nag
6,063,221 A 5/2000 Weinberg et al.
6,071,580 A * 6/2000 Bland et al. ................ 428/36.5
6,074,578 A 6/2000 Csongor et al.
6,086,540 A * 7/2000 Bonneville .......... A61K 49/223 600/458
6,106,473 A * 8/2000 Violante et al. ............. 600/458
6,110,444 A 8/2000 Klaveness et al.
6,165,165 A 12/2000 Cecchi et al.
6,207,752 B1 * 3/2001 Abraham et al. .............. 525/67
6,210,330 B1 4/2001 Tepper
6,240,960 B1 6/2001 Fillmore
6,261,241 B1 7/2001 Burbank et al.
6,277,084 B1 8/2001 Abele et al.
6,283,951 B1 9/2001 Flaherty et al.
6,290,672 B1 * 9/2001 Abae ....................... 604/101.04
6,306,094 B1 10/2001 Joseph
6,312,429 B1 11/2001 Burbank et al.
6,331,166 B1 12/2001 Burbank et al.
6,344,026 B1 2/2002 Burbank et al.
6,346,086 B1 2/2002 Maksem et al.
6,347,241 B2 2/2002 Burbank et al.
6,356,782 B1 3/2002 Sirimanne et al.
6,358,211 B1 3/2002 Mamayek
6,364,855 B1 * 4/2002 Zappala .............. A61N 5/1027 604/48
6,371,904 B1 4/2002 Sirimanne et al.
6,371,973 B1 4/2002 Tepper
6,427,081 B1 7/2002 Burbank et al.
6,432,352 B1 8/2002 Csongor
6,435,189 B1 8/2002 Lewis et al.
6,454,727 B1 9/2002 Burbank et al.
6,461,302 B1 10/2002 Thompson
6,471,700 B1 10/2002 Burbank et al.
6,481,462 B2 11/2002 Fillmore et al.
6,497,706 B1 12/2002 Burbank et al.
6,506,156 B1 * 1/2003 Jones et al. .................. 600/439
6,508,773 B2 1/2003 Burbank et al.
6,517,498 B1 2/2003 Burbank et al.
6,527,752 B1 3/2003 Bosley, Jr. et al.
6,540,693 B2 4/2003 Burbank et al.
6,540,695 B1 4/2003 Burbank et al.
6,544,185 B2 4/2003 Montegrande
6,544,230 B1 4/2003 Flaherty et al.
6,567,689 B2 5/2003 Burbank et al.
6,577,904 B1 6/2003 Zhang et al.
6,610,005 B1 8/2003 Tao
6,610,016 B1 * 8/2003 Violante et al. ............. 600/458
6,638,234 B2 10/2003 Burbank et al.
6,656,407 B1 12/2003 Halgren et al.
6,659,105 B2 12/2003 Burbank et al.
6,662,041 B2 12/2003 Burbank et al.
6,673,440 B2 1/2004 Douglas et al.
6,676,658 B2 1/2004 Burbank et al.
6,679,824 B1 1/2004 Reed et al.
6,679,851 B2 1/2004 Burbank et al.
6,685,648 B2 2/2004 Flaherty et al.
6,689,071 B2 2/2004 Burbank et al.
6,695,767 B2 2/2004 Martinez Garcia et al.
6,695,787 B2 2/2004 Hogendijk et al.
6,699,206 B2 3/2004 Burbank et al.
6,712,775 B2 3/2004 Burbank et al.
6,716,179 B2 4/2004 Burbank et al.
6,723,052 B2 * 4/2004 Mills ............................ 600/459
6,725,083 B1 4/2004 Burbank et al.
6,736,409 B2 5/2004 Hollenberg
6,749,554 B1 6/2004 Snow et al.
6,758,848 B2 7/2004 Burbank et al.
6,761,680 B2 7/2004 Terwilliger et al.
6,786,858 B2 9/2004 Terwilliger et al.
6,838,278 B2 1/2005 Fortino
6,840,090 B2 * 1/2005 Smith ........................... 73/49.8
6,860,856 B2 3/2005 Ward et al.
6,862,470 B2 3/2005 Burbank et al.
6,875,168 B2 4/2005 Bateman et al.
6,875,182 B2 4/2005 Wardle et al.
6,905,458 B2 6/2005 Choay et al.
6,958,044 B2 10/2005 Burbank et al.
6,993,375 B2 1/2006 Burbank et al.
6,996,433 B2 2/2006 Burbank et al.
6,997,885 B2 2/2006 Lubock et al.
7,014,610 B2 * 3/2006 Koulik .......................... 600/462
7,047,063 B2 5/2006 Burbank et al.

(56) References Cited

U.S. PATENT DOCUMENTS 7,060,020 B2 6/2006 Terwilliger et al.
7,188,537 B2 3/2007 Junger
7,189,206 B2 3/2007 Quick et al.
7,229,413 B2 6/2007 Violante et al.
7,229,418 B2 6/2007 Burbank et al.
7,229,439 B2 6/2007 Burbank et al.
7,235,052 B2 6/2007 Kellar et al.
7,258,669 B2 * 8/2007 Russell .................. A61B 90/39 600/439
7,261,712 B2 8/2007 Burbank et al.
7,264,596 B2 9/2007 Burbank et al.
7,282,034 B2 10/2007 Burbank et al.
7,322,938 B2 1/2008 Burbank et al.
7,322,939 B2 1/2008 Burbank et al.
7,322,940 B2 1/2008 Burbank et al.
7,329,228 B2 2/2008 Burbank et al.
7,357,794 B2 4/2008 Makower er al.
7,357,801 B2 4/2008 Burbank et al.
7,377,902 B2 5/2008 Burbank et al.
7,382,857 B2 6/2008 Engel
7,384,391 B2 6/2008 Spittle et al.
7,470,249 B2 12/2008 Junger
7,488,295 B2 2/2009 Burbank et al.
7,565,191 B2 7/2009 Burbank et al.
7,625,347 B2 12/2009 Burbank et al.
7,637,904 B2 12/2009 Wingler et al.
7,651,467 B2 1/2010 Lubock et al.
7,651,505 B2 1/2010 Lubock et al.
7,668,582 B2 2/2010 Sirimanne et al.
7,736,337 B2 6/2010 Diep et al.
7,792,569 B2 9/2010 Burbank et al.
7,794,402 B2 9/2010 Wang
7,819,819 B2 10/2010 Quick et al.
7,867,169 B2 1/2011 Webler et al.
7,879,011 B2 2/2011 Chang
7,887,737 B2 2/2011 Mejlhede et al.
7,970,454 B2 6/2011 Jones et al.
7,983,734 B2 7/2011 Jones et al.
8,052,669 B2 11/2011 Lee-Sepsick et al.
8,092,390 B2 * 1/2012 Field ................... A61B 17/435 600/458
8,137,346 B2 3/2012 Burbank et al.
8,147,487 B2 4/2012 Burbank et al.
8,152,737 B2 4/2012 Burbank et al.
8,177,792 B2 5/2012 Lubock et al.
8,200,313 B1 6/2012 Rambod et al.
8,219,182 B2 7/2012 Burbank et al.
8,224,424 B2 7/2012 Burbank et al.
8,229,553 B2 7/2012 Burbank et al.
8,273,009 B2 9/2012 Arabia et al.
8,282,573 B2 10/2012 Shabaz et al.
8,303,509 B2 11/2012 Webler et al.
8,306,602 B2 11/2012 Sirimanne et al.
8,320,993 B2 11/2012 Sirimanne et al.
8,320,994 B2 11/2012 Sirimanne et al.
8,343,071 B2 1/2013 Shabaz et al.
8,360,990 B2 1/2013 Shabaz et al.
8,361,082 B2 1/2013 Jones et al.
8,377,109 B2 2/2013 Vrba et al.
8,382,674 B2 2/2013 Webler
8,398,596 B2 3/2013 Field
8,430,863 B2 4/2013 Webler
8,460,204 B2 6/2013 Quick et al.
8,465,412 B2 6/2013 Kamrava
8,498,693 B2 7/2013 Jones et al.
8,560,052 B2 10/2013 Mills
8,585,596 B1 11/2013 Flaherty et al.
8,600,481 B2 12/2013 Sirimanne et al.
8,603,121 B2 12/2013 Surti et al.
8,622,887 B2 1/2014 Gergeley
8,626,269 B2 1/2014 Jones et al.
8,626,270 B2 1/2014 Burbank et al.
8,633,023 B2 1/2014 Du et al.
8,636,734 B2 1/2014 Burbank et al.
8,656,928 B2 2/2014 Carlson et al.
8,663,116 B2 3/2014 Hamilton, Jr.
8,672,892 B2 3/2014 Carr et al.
8,690,752 B2 4/2014 Jose
8,718,745 B2 5/2014 Burbank et al.
8,784,433 B2 7/2014 Lubock et al.
8,795,452 B2 8/2014 Alpert et al.
8,834,370 B2 9/2014 Evert et al.
8,880,154 B2 11/2014 Jones et al.
8,936,553 B2 1/2015 Stigall et al.
8,951,195 B2 2/2015 Sheldon et al.
8,959,753 B2 2/2015 Garbini et al.
8,965,486 B2 2/2015 Burbank et al.
9,033,889 B2 5/2015 Hamilton, Jr.
9,034,363 B2 5/2015 Doshi et al.
9,044,162 B2 6/2015 Jones et al.
9,044,215 B2 6/2015 Shabaz et al.
9,085,097 B2 7/2015 Lentz et al.
9,107,640 B2 8/2015 Ho et al.
9,149,341 B2 10/2015 Jones et al.
9,179,935 B2 11/2015 Zamescu et al.
9,204,866 B2 12/2015 Shabaz et al.
9,216,012 B2 12/2015 Burbank et al.
9,216,037 B2 12/2015 Buster et al.
9,220,880 B2 12/2015 Lee-Sepsick et al.
9,237,937 B2 1/2016 Burbank et al.
9,242,076 B2 1/2016 Burton et al.
9,247,960 B2 2/2016 Carson et al.
9,320,540 B2 4/2016 Badie
9,636,082 B2 * 5/2017 Field .................... A61B 17/435
9,642,591 B2 * 5/2017 Field .................... A61B 17/435
2002/0026117 A1 2/2002 Joseph
2002/0134850 A1 9/2002 Hollenberg
2002/0177776 A1 * 11/2002 Crawford Kellar . A61B 8/0833 600/458
2003/0032896 A1 * 2/2003 Bosley, Jr. ........... A61B 17/435 600/585
2003/0040756 A1 2/2003 Field
2003/0050531 A1 3/2003 Field
2003/0206864 A1 11/2003 Mangin
2003/0208101 A1 11/2003 Cecchi
2004/0230119 A1 * 11/2004 Brustad et al. ............... 600/442
2005/0074406 A1 4/2005 Couvillon, Jr. et al.
2005/0143656 A1 6/2005 Burbank et al.
2006/0089608 A1 * 4/2006 Shaykh ................ A61B 17/435 604/264
2006/0095015 A1 * 5/2006 Hobbs .................. A61B 18/245 604/508
2006/0106338 A1 5/2006 Chang
2007/0167822 A1 7/2007 Webler et al.
2007/0179575 A1 8/2007 Esch et al.
2007/0255140 A1 11/2007 Violante et al.
2007/0265516 A1 11/2007 Wang
2008/0058702 A1 3/2008 Arndt et al.
2008/0154136 A1 6/2008 Webler
2010/0256577 A1 * 10/2010 Field .................. A61B 17/3403 604/272
2010/0331955 A1 * 12/2010 Vrba et al. ................... 623/1.11
2013/0281835 A1 * 10/2013 Field .................... A61B 8/0833 600/424

FOREIGN PATENT DOCUMENTS

DE 40 14 998 11/1991
DE 299 08 256 7/1999 ............... A61B 8/14
DE 197 27 740 9/1999 ............... A61B 8/12
EP 0033659 2/1981
EP 0 072 671 2/1983 ............. A61B 10/00
EP 0 083 973 7/1983 ............. A61B 10/00
EP 0 109 657 5/1984 ............ A61M 25/00
EP 0 131 166 1/1985 ............... A61M 1/00
EP 0 243 341 10/1987 .............. A61M 5/14
EP 0 323 527 7/1989 .............. A61M 1/00
EP 0 356 774 3/1990 ............ A61M 25/00
EP 0 382 392 8/1990 ............. A61B 19/00
EP 0 386 936 9/1990 ............... A61B 8/08
EP 0 481 685 4/1992 ............. A61B 19/00
EP 0 526 669 2/1993 ............ A61M 25/00
EP 0 552 924 7/1993 ............... A61B 8/08

(56) References Cited

FOREIGN PATENT DOCUMENTS

| | | | |
|---|---|---|---|
| EP | 0 567 285 | 10/1993 | ............ A61M 25/00 |
| EP | 0 586 056 | 3/1994 | ........... A61B 17/425 |
| EP | 0 624 342 | 11/1994 | |
| EP | 0 935 442 | 8/1999 | ............... A61B 8/00 |
| EP | 0 941 128 | 9/1999 | ............. A61K 49/00 |
| EP | 0 995 459 | 4/2000 | ............ A61M 25/00 |
| EP | 0 996 363 | 5/2000 | ............... A61B 8/00 |
| EP | 1 105 170 | 6/2001 | ............. A61L 31/00 |
| EP | 1 109 496 | 6/2001 | ............. A61B 10/00 |
| EP | 1 132 049 | 9/2001 | ............... A61B 8/08 |
| EP | 1 139 878 | 10/2001 | ............. A61B 17/00 |
| EP | 1 146 910 | 10/2001 | ............. A61K 49/00 |
| EP | 1 152 696 | 11/2001 | ............. A61B 17/00 |
| EP | 1 155 418 | 11/2001 | ............... G21G 4/08 |
| EP | 1 118 337 | 1/2002 | |
| EP | 1 166 720 | 1/2002 | ............. A61B 10/00 |
| EP | 1 173 096 | 1/2002 | ............... A61B 8/08 |
| EP | 1 177 776 | 2/2002 | ............. A61D 19/02 |
| EP | 1 189 546 | 3/2002 | ............. A61B 19/00 |
| EP | 1 196 107 | 4/2002 | ............. A61B 19/00 |
| EP | 1 274 353 | 1/2003 | ........... A61B 17/435 |
| EP | 1 358 856 | 11/2003 | ............. A61D 19/02 |
| EP | 1 450 891 | 9/2004 | ............... A61N 5/10 |
| EP | 1 491 147 | 12/2004 | ............. A61B 17/00 |
| EP | 1 494 721 | 1/2005 | ............. A61B 19/00 |
| EP | 1 513 581 | 3/2005 | ............ A61M 37/00 |
| EP | 1 525 856 | 4/2005 | ............. A61B 19/00 |
| EP | 1 599 125 | 11/2005 | ............. A61B 10/00 |
| EP | 1 626 667 | 2/2006 | ............. A61B 19/00 |
| EP | 1 667 589 | 6/2006 | ............. A61B 17/43 |
| EP | 1 696 800 | 9/2006 | ............. A61B 10/00 |
| EP | 1 781 178 | 5/2007 | ............. A61B 10/00 |
| EP | 1 919 388 | 5/2008 | ............ A61M 37/00 |
| EP | 1 967 147 | 9/2008 | ............. A61B 17/34 |
| EP | 2 103 266 | 9/2009 | ........... A61B 17/435 |
| EP | 2 114 270 | 11/2009 | ........... A61B 17/435 |
| EP | 2 174 596 | 4/2010 | ............. A61B 17/00 |
| EP | 2 319 449 | 5/2011 | ............. A61B 90/00 |
| EP | 2 389 868 | 11/2011 | ............. A61B 10/00 |
| EP | 2 407 111 | 1/2012 | ............. A61B 10/02 |
| EP | 2 407 119 | 1/2012 | ............. A61B 19/00 |
| EP | 2 517 630 | 10/2012 | ............... A61B 8/12 |
| EP | 2 555 687 | 2/2013 | ............. A61B 10/02 |
| EP | 2 564 890 | 3/2013 | ............ A61M 25/10 |
| EP | 2 570 150 | 3/2013 | ............ A61M 25/10 |
| EP | 2 620 111 | 7/2013 | ............. A61B 17/34 |
| EP | 2 641 546 | 9/2013 | ............. A61B 10/02 |
| EP | 2 984 991 | 2/2016 | ............. A61B 10/02 |
| EP | 2 995 260 | 3/2016 | ............. A61B 10/02 |
| FR | 2 716 266 | 8/1995 | ............. G01S 15/02 |
| GB | 829383 | 3/1960 | |
| GB | 894653 | 4/1962 | |
| GB | 1151222 | 5/1969 | .............. A61M 5/28 |
| GB | 2 263 642 | 8/1995 | ............ A61M 25/01 |
| GB | 2 274 991 | 10/1996 | ............ A61M 25/00 |
| GB | 2 379 610 | 3/2003 | |
| GB | 2 381 198 | 4/2003 | ............ A61M 25/01 |
| GB | 2 388 784 | 11/2003 | ........... A61B 17/435 |
| GB | 2 380 944 | 10/2004 | .......... A61M 25/095 |
| GB | 2494395 | 1/2014 | ............ A61M 25/10 |
| GB | 2494864 | 2/2014 | ............ A61M 25/10 |
| GB | 2469839 | 9/2014 | ............... A61B 8/00 |
| JP | 58-92951 | 6/1983 | |
| SU | 1255450 | 9/1986 | ............. B29C 47/12 |
| WO | WO 94/17743 | 8/1994 | ........... A61B 17/435 |
| WO | WO 95/23615 | 9/1995 | ............. A61K 49/00 |
| WO | 98/19713 | 5/1998 | |
| WO | WO 99/03399 | 1/1999 | ............... A61B 8/00 |
| WO | 00/09178 | 2/2000 | |
| WO | WO 02/02171 | 1/2002 | ............ A61M 25/00 |

OTHER PUBLICATIONS

Hale, Lyndon, "Embryo transfer: how to ensure correct placement in utero", *Reproduction, Fertility and Development*, vol. 13, pp. 95-98 (2001).

Strickler, Ronald C. et al., "Ultrasound guidance for human embryo transfer", *Fertility and Sterility*, vol. 43, No. 1, pp. 54-61 (Jan. 1985).

Wood, Ellen G. et al., "Ultrasound-guided soft catheter embryo transfers will improve pregnancy rates in in-vitro fertilization", *Human Reproduction*, vol. 15, No. 1, pp. 107-112 (2000).

Woolcott, Robert et al., "Potentially important variables identified by transvaginal ultrasound-guided embryo transfer", *Human Reproduction*, vol. 12, No. 5, pp. 963-966 (1997).

* cited by examiner

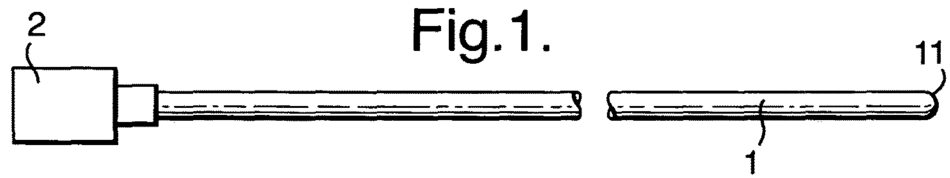
Fig.1.
2
11
1
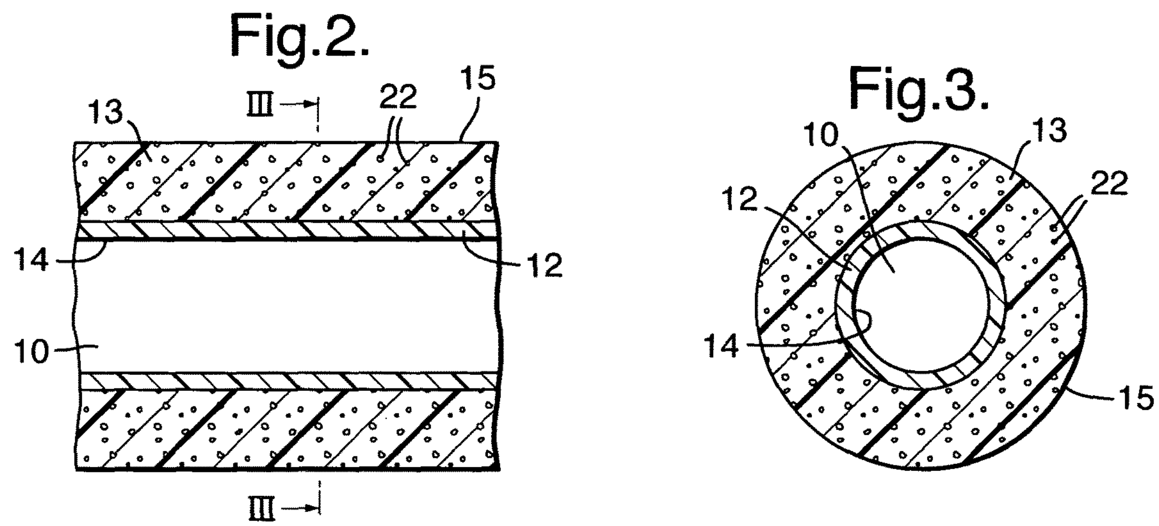
Fig.2.
13
III
22
15
14
12
10
III
Fig.3.
10
13
12
22
14
15
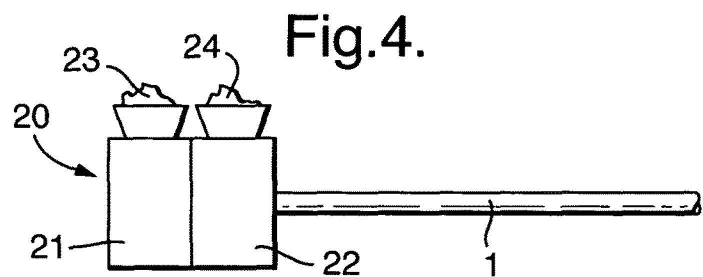
Fig.4.
23
24
20
21
22
1
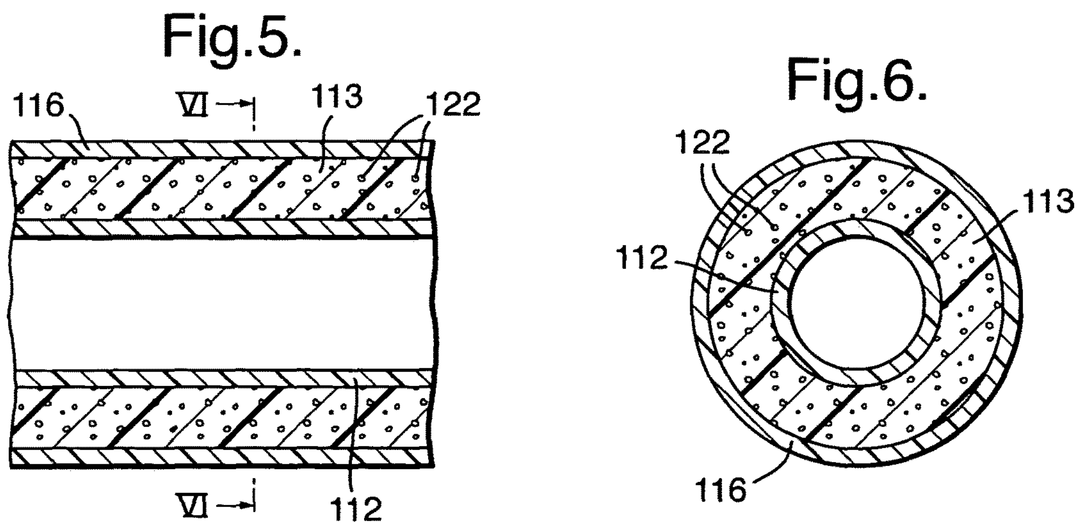
Fig.5.
116
VI
113
122
112
VI
Fig.6.
122
113
112
116

MEDICAL DEVICES

BACKGROUND OF THE INVENTION

This invention relates to medical devices.

The invention is more particularly concerned with catheters or the like, that are visible under ultrasound observation.

Ultrasound imaging equipment is increasingly being used during surgical procedures to monitor the location of a device within the body. The visibility of a device under ultrasound depends on various factors including the difference between the acoustic impedance of the material of the device and that of the surrounding medium, such as the patient tissue or body fluid within which the device is located. This difference is relatively low with plastic devices such as catheters and may make conventional catheters difficult to locate. Even devices of metal, such as needles, present problems of visibility under ultrasound observation because of the directional nature of the reflections. In some orientations a metal needle may be clearly visible but in other orientations it may be considerably less visible.

Attempts have been made to increase the visibility of medico-surgical devices under ultrasound observation in various ways. The surface of the device may be modified, such as by forming grooves or indentations in its surface. A reflective coating may be applied to the device, such as incorporating bubbles, as described in WO98/19713 and EP0624342. Alternatively, a metal marker may be secured to a plastics catheter. GB2379610 describes a catheter where the wall is made entirely of a plastics including gas bubbles or where bubble-containing material is in a stripe occupying only a part of the circumference. Although this latter form of catheter has various advantages, it has been found that there is a tendency for the surface of the bore through the catheter to be interrupted by small protrusions where the bubbles break the surface. In some applications, such as for embryo transfer, it is important that the bore of the catheter is as smooth as possible so any interruption of this is a disadvantage. In other applications it may be important instead for the outer surface to be as smooth as possible, or for both the outer and inner surface to be smooth.

BRIEF SUMMARY OF THE INVENTION

It is an object of the present invention to provide an alternative medical device.

According to the present invention there is provided a medical device having an elongate portion of plastics material, the portion being extruded with at least a first, inner layer and a second layer on the outside of the inner layer, one of the layers being substantially free of gas bubbles and the other of the layers including gas bubbles dispersed within it to increase the visibility of the device under ultrasound imaging.

The layer substantially free of gas bubbles may be thinner than the other layer. The layer substantially free of gas bubbles may be the inner layer. The second layer may provide an outer surface of the catheter. The device may include a third layer on the outside of the second layer. The second layer may contain gas bubbles and the first and third layers may be substantially free of gas bubbles. The bubbles may be in a region extending around the entire circumference of the device. The bubbles preferably extend in a continuous region along the length of the device. The gas bubbles may have a size in the range 0.1μ to 300μ, preferably having a size in the range 1μ to 50μ and most preferably having a size in the range 5μ to 10μ. The gas bubbles may be provided by gas-filled polymer microspheres. The device may be a catheter having a bore extending along its length. The inner layer may have an inner surface providing the bore of the catheter. The plastics material is preferably transparent to the eye, the density of bubbles being such as to permit material within the catheter to be viewed by the eye.

An embryo-transfer catheter and its method of manufacture, according to the present invention, will now be described, by way of example, with reference to the accompanying drawing.

BRIEF DESCRIPTION OF THE DRAWING

FIG. 1 is a side elevation view of the catheter;

FIG. 2 is a sectional side elevation view of a part of the catheter of FIG. 1 to a larger scale;

FIG. 3 is a cross-section view of the catheter along the line III-III of FIG. 2;

FIG. 4 illustrates schematically manufacture of the catheter;

FIG. 5 is a sectional side elevation view of a part of an alternative catheter; and FIG. 6 is a cross-section view of the catheter of FIG. 5 along the line VI-VI.

DETAILED DESCRIPTION OF THE PREFERRED EMBODIMENTS

With reference first to FIGS. 1 to 3, the catheter comprises an elongate portion in the form of a flexible shaft 1 and a hub 2 joined at the rear end of the shaft. The shaft 1 has a circular section and a bore 10 extending along its length. The shaft 1 opens at its forward, right-hand, patient end 11, which is a traumatically rounded.

The shaft 1 is extruded in two layers 12 and 13. The first, inner layer 12 is of a clear, transparent polyurethane material and is free of gas bubbles so that its inner surface 14, providing the surface of the bore 10, is completely smooth. The second layer 13 is formed around the entire circumference of the first layer 12 and its outer surface 15 provides the outer surface of the catheter. The second layer 13 incorporates small, gas-filled bubbles 22 the size and distribution of which are selected to increase the visibility of the catheter under ultrasound observation. Typically, the gas bubbles have a diameter in the range of about 0.1μ to 300μ, preferably being between 1μ and 50μ with the most preferred range being about 5μ to 10μ. The bubbles 22 extend uniformly through the thickness and around the circumference of the second layer 13 and may be spherical or of any other regular or irregular shape. The second layer 13 is preferably made from the same plastics material as the first layer and the gas bubbles are preferably provided by incorporating gas-filled polymer microspheres such as of the kind sold under the trade mark Expancel ("Expancel" is a registered trade mark of Akzo Nobel). The bubble-filled layer 13 is preferably as thick as possible so as to increase the visibility of the catheter under ultrasound observation. The inner layer 12 may be relatively thin since its purpose is solely to provide a smooth inner surface for the catheter.

The hub 2 serves to make connection with the shaft 1 and is moulded from a rigid, transparent plastics material, being subsequently bonded with the rear end of the shaft.

The shaft 1 is extruded in the manner shown in FIG. 4 using an extrusion machine 20. The machine 20 has two extrusion heads 21 and 22, which are supplied respectively with a polyurethane material 23 and with a polyurethane material 24 containing hollow microspheres. The two materials 23 and 24 are heated and supplied to the respective extrusion heads 21 and 22 so that tubing is formed with the bubble-filled material 24 coextruded as the outer layer 13 about the outside of the inner layer 12, which is of the bubble-free material 23. The shaft 1 can be extruded continuously at low cost, without the need for any subsequent operations apart from attaching the hub 2 and end forming the patient end tip 11.

The bubbles could be formed in various other ways, such as by injecting gas into the melt. Alternatively, chemical foaming agents could be added to the plastics material, such as: azocarbonomides, dinitrosopentmethelyene-tetramine, benzenephonohydrazine, 4,4 oxybis(benzenephonohydrazine), $NN^1$dimethyl-$NN^1$dinitrosoterephthalamide, azoisobutyronitrile, sodium bicarbonate, terephthalazide or trihydrazinatrazine. Another way of forming the gas bubbles would be by incorporating a liquid into the plastics melt which volatises during the melt process. Alternatively, solid powdered dry ice (carbon dioxide) could be incorporated into the melt so that the particles of dry ice become gas bubbles during the forming process. It might be possible to use other solids which undergo sublimation in this way. The bubbles could be formed directly as a result of chemical reaction during polymerisation and or alternatively during cross-linking. The bubbles could be formed mechanically by whipping the plastics in a liquid form, such as in the manner used to form latex foam. Alternatively, small particles of a soluble material could be added to the plastics melt and subsequently dissolved away.

The bubble-filled layer need not provide the outer surface of the catheter, especially where the outer surface of the catheter needs to be smoother than can be provided by a bubble layer. Instead, as shown in FIGS. 5 and 6, the bubble-filled layer 113 could be sandwiched between an inner layer 112 and a third, outer layer 116, the inner and outer layers being of the same material and being free of bubbles. Preferably, the inner layer 112 and the outer layer 116 are relatively thin and the middle, bubble-filled layer 113 is relatively thick, to maximise the ultrasound reflecting properties of the catheter. This three-layer tube is also made by co-extruding the three layers with one another. Alternatively, where it was necessary for the outer surface of the catheter to be smooth and there was no need for the bore to be smooth, the catheter could just have two layers where the outer layer was thin and bubble-free and the inner layer was thicker and contained bubbles.

The catheter could have any number of additional layers with one or more layers containing bubbles.

Catheters according to the present invention can be made having good visibility under ultrasound imaging without producing multiple echoes. They can produce a good image regardless of the orientation of the catheter shaft. The shaft can be made sufficiently transparent to ultrasound energy to enable material flowing along the bore of the catheter to be observed on the ultrasound image.

Because the catheter does not require any coating or separate marker there is no need for subsequent assembly operations and there is no risk of detachment. The catheter can be made of conventional, medically-approved materials so does not present any new risk to the patient. The outer surface of the three-layer catheter can be smooth so the catheter can be inserted or slid through an outer tube with low friction. A smooth bore can be provided to a catheter to ensure free flow along the bore, which can be important where the catheter is used to transfer embryos. In other applications, a smooth inner surface may reduce the accumulation of biofilm in the catheter. The catheter can be made without the need for metal components, which can be an advantage where the catheter is used while the patient is being viewed by magnetic imaging techniques. The catheter can be completely transparent to x-rays or the plastics from which it is formed could incorporate an x-ray opaque filler, such as barium sulphate.

The bubble size and density can be selected so that the optical transparency of the plastics forming the shaft remains sufficient to enable material flowing along the shaft to be viewed by the eye.

It is not essential for the bubbles to be provided around the entire circumference of the bubble-containing layer, instead, the bubbles could just be provided along a longitudinal stripe in the layer. This arrangement can be used where the shaft needs to have increased clarity so that material within the catheter can be seen by the eye. Alternatively, the bubbles could be contained around the entire circumference of the layer apart from a bubble-free longitudinal strip. The bubble region need not be continuous along the length of the catheter. Instead, discrete separate regions with bubbles could be separated from one another along the length of the catheter by regions without bubbles. A shaft for such a catheter could be made by blowing gas into the plastics forming the bubble layer and by interrupting the gas flow. Where the bubbles are contained within a stripe, this could be interrupted to make it discontinuous by extruding the stripe using two auxiliary extruders, one having material with hollow microspheres and the other having material without the microspheres. Alternate extruders would be switched on and off so that the stripe could have sections containing bubbles separated from one another by sections without bubbles. A catheter having a layer with an interrupted bubble region may give a clearer ultrasound indication of movement of the catheter along its length and may also enable clearer observation of material flowing along the catheter both by ultrasound and by the eye.

The invention is not confined to catheters but could be used in other medical devices such as cables and medical devices without a bore, or with more than one bore.

What we claim is:

1. An embryo transfer catheter having an elongate shaft comprising a first, inner layer of a polymeric material coextruded with a second layer of a polymeric material on an outside of the inner layer, the first layer being substantially free of gas bubbles, the second layer including fixed gas bubbles encapsulated by the polymeric material of the second layer to increase the visibility of the catheter under ultrasound imaging, the gas bubbles being in a region extending along the length of the elongate shaft of the catheter, and the first layer that is substantially free of gas bubbles being thinner than the second layer and forming an innermost layer of the elongate shaft of the catheter.

2. The embryo transfer catheter according to claim 1, wherein the gas bubbles have a size in the range 1μ to 50μ.

3. The embryo transfer catheter according to claim 2, wherein the gas bubbles have a size in the range 5μ to 10μ.

4. The embryo transfer catheter of claim 1, wherein the gas bubbles have a size in the range 0.1μ to 300μ.

5. The embryo transfer catheter according to claim 1, wherein the second layer forms an outermost layer of the elongate shaft of the catheter.

6. The embryo transfer catheter according to claim 1, wherein the region including the gas bubbles extends around the entire circumference of the elongate shaft of the catheter.

7. The embryo transfer catheter according to claim 1, wherein the region including the gas bubbles extends continuously along the length of the elongate shaft of the catheter.

8. The embryo transfer catheter according to claim 1, wherein the gas bubbles are provided by gas filled polymer microspheres.

9. The embryo transfer catheter according to claim 1, wherein the catheter has a bore extending along its length.

10. The embryo transfer catheter according to claim 9, wherein the inner layer has an inner surface defining the bore of the catheter.

11. The embryo transfer catheter according to claim 9, wherein the polymeric materials are transparent to the eye, and the density of the gas bubbles is such as to permit material within the catheter to be viewed by the eye.

12. The embryo transfer catheter according to claim 1, wherein the region including the gas bubbles extends in a longitudinal stripe along the elongate shaft of the catheter.

13. An embryo transfer catheter having an elongate shaft of polymeric material, the shaft comprising an inner layer of a polymeric material and an outer layer of a polymeric material on an outside of the inner layer, the inner layer being substantially free of gas bubbles, the outer layer including fixed gas bubbles encapsulated by the polymeric material of the outer layer to increase the visibility of the catheter under ultrasound imaging, the gas bubbles being in a region extending along the length of the elongate shaft of the catheter, the outer layer being thicker than the inner layer, and the inner layer forming an innermost layer of the elongate shaft of the catheter.

14. The embryo transfer catheter according to claim 13, wherein the region including the gas bubbles extends around the entire circumference of the elongate shaft of the catheter.

15. The embryo transfer catheter according to claim 13, wherein the region including the gas bubbles extends continuously along the length of the elongate shaft of the catheter.

16. The embryo transfer catheter according to claim 13, wherein the region including the gas bubbles extends in a longitudinal stripe along the elongate shaft of the catheter.

17. An embryo transfer catheter having an elongate shaft of transparent polymeric material, the shaft comprising an inner layer of a polymeric material coextruded with an outer layer of a polymeric material on an outside of the inner layer, the inner layer being substantially free of gas bubbles, the inner surface of the outer layer being covered by the inner layer, the outer layer including fixed gas bubbles encapsulated by the polymeric material of the outer layer to increase the visibility of the catheter under ultrasound imaging, the gas bubbles being in a region extending along the length of the elongate shaft of the catheter, the density of the gas bubbles being sufficiently low to enable visualization of an embryo in the catheter, the outer layer being thicker than the inner layer, and the inner layer forming an innermost layer of the elongate shaft of the embryo transfer catheter.

18. The embryo transfer catheter according to claim 17, wherein the region including the gas bubbles extends around the entire circumference of the elongate shaft of the catheter.

19. The embryo transfer catheter according to claim 17, wherein the region including the gas bubbles extends continuously along the length of the elongate shaft of the catheter.

20. The embryo transfer catheter according to claim 17, wherein the region including the gas bubbles extends in a longitudinal stripe along the elongate shaft of the catheter.

21. An embryo transfer catheter having an elongate shaft of polymeric material, the shaft comprising three coextruded layers each of a polymeric material, the three coextruded layers comprising an inner layer, an outer layer and a middle layer between the inner and outer layers such that the inner and outer surfaces of the middle layer are covered by the inner and outer layers, respectively, the inner and outer layers being substantially free of gas bubbles, the middle layer including fixed gas bubbles encapsulated by the polymeric material of the middle layer to increase the visibility of the catheter under ultrasound imaging, the gas bubbles being in a region extending along the length of the elongate shaft of the catheter, the inner and outer layers being thinner than the middle layer, and the inner and outer layers forming inner and outer surfaces, respectively, of the elongate shaft of the catheter.

* * * * *